United States Patent
Frausto et al.

(10) Patent No.: US 11,839,737 B2
(45) Date of Patent: Dec. 12, 2023

(54) SELF-ADJUSTING IV STAND

(71) Applicant: CareFusion 303, Inc., San Diego, CA (US)

(72) Inventors: Tomas Frausto, Walnut, CA (US); Jason Andrew Wine, Placentia, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 17/714,894

(22) Filed: Apr. 6, 2022

(65) Prior Publication Data

US 2022/0387704 A1 Dec. 8, 2022

Related U.S. Application Data

(60) Provisional application No. 63/196,024, filed on Jun. 2, 2021.

(51) Int. Cl.
*A61M 5/14* (2006.01)

(52) U.S. Cl.
CPC ....... *A61M 5/1415* (2013.01); *A61M 2205/10* (2013.01); *A61M 2205/3389* (2013.01); *A61M 2205/3393* (2013.01)

(58) Field of Classification Search
CPC ............ A61M 5/1415; A61M 2205/10; A61M 2205/3389; A61M 2205/3393
USPC ...................................................... 248/125.8
See application file for complete search history.

(56) References Cited

U.S. PATENT DOCUMENTS

| | | | | |
|---|---|---|---|---|
| 5,112,019 A | * | 5/1992 | Metzler | A61M 3/0266 248/176.1 |
| 8,336,839 B2 | * | 12/2012 | Boccoleri | A61M 5/1415 248/280.11 |
| 10,463,784 B2 | * | 11/2019 | Massengill | A61M 5/1415 |
| 10,827,829 B1 | * | 11/2020 | Labrosse | A47B 21/06 |
| 11,217,340 B2 | * | 1/2022 | Desch | A61M 5/172 |
| 2016/0228639 A1 | * | 8/2016 | Zin | A61M 5/16813 |

FOREIGN PATENT DOCUMENTS

| | | |
|---|---|---|
| CN | 106377815 A | 2/2017 |
| CN | 108355192 A | 8/2018 |
| CN | 110496265 A | 11/2019 |

OTHER PUBLICATIONS

International Search Report and Written Opinion for Application No. PCT/US2022/028382, dated Aug. 8, 2022, 14 pages.

* cited by examiner

*Primary Examiner* — Nkeisha Smith
(74) *Attorney, Agent, or Firm* — Morgan, Lewis & Bockius LLP (57) ABSTRACT

IV stand assemblies are provided that include a base, a stand, a platform and a motorized pole assembly having a housing, a pole and a drive. The drive moves the pole to extend and retract the pole relative to the housing. A weight measurement assembly measures weight of a fluid within a fluid container hanging from the IV stand assembly. IV stand assemblies with a pulley/belt assembly and methods of operating IV assemblies are also provided.

11 Claims, 7 Drawing Sheets

SELF-ADJUSTING IV STAND

CROSS-REFERENCE TO RELATED APPLICATIONS

This application claims the benefit of priority under 35 U.S.C. § 119 to U.S. Provisional Patent Application Ser. No. 63/196,024, entitled "SELF-ADJUSTING IV STAND," filed on Jun. 2, 2021, the entirety of which is incorporated herein by reference.

TECHNICAL FIELD

The present disclosure generally relates to intravenous (IV) stands, and in particular self-adjusting IV stands.

BACKGROUND

Typical infusion or IV sets are connected to fluid sources such as IV bags, bottles or other containers, which are hung from a standard IV pole. The IV pole has one or more hooks to hang the IV bags and may be either stationary or have a wheeled base. Some typical IV poles are one size fits all and are not height adjustable. Thus, these static IV poles do not allow for the ability to control the head-height or pressure inside the IV set via the IV pole. Also, a static IV pole cannot be lowered for ease of loading and unloading IV bags to/from the IV pole. Some typical IV poles are manually adjustable, where they can be raised and lowered by loosening a knob. However, none of the above-described typical IV poles have any sensors for detecting the weight or fluid level of a hung IV bag.

For these reasons, it is desirable to provide devices and methods for providing self-adjusting motor driven IV poles with integrated weight measurement devices to reduce user fatigue during loading/unloading, to control flow rate through the IV set by adjusting the head height and to monitor the amount of fluid/infusate currently hanging on the IV pole.

SUMMARY

One or more embodiments of an IV stand assembly include a base, a stand coupled to the base, a platform disposed at an end of the stand and a motorized pole assembly coupled to the platform. The motorized pole assembly includes a housing, a pole movably coupled to the housing and a drive coupled to the pole, the drive configured to move the pole to extend and retract the pole relative to the housing. The IV stand assembly also includes a weight measurement assembly coupled to the pole assembly, the weight measurement assembly configured to measure weight of a fluid within a fluid container hanging from the IV stand assembly.

One or more embodiments of an IV stand assembly include a base and a stand coupled to the base, the stand including an internal channel and a retainer channel. The IV stand assembly also includes a pulley/belt assembly disposed within the internal channel of the stand, the pulley/belt assembly including a pulley and a belt. The IV stand assembly further includes a retainer coupled to the belt, the retainer movably disposed within the retainer channel and a drive coupled to the belt, the drive configured to move the belt relative to the pulley to cause the retainer to move along the retainer channel.

One or more embodiments of a method of operating an IV stand assembly include hanging a fluid container on a retainer of the IV stand assembly; moving, by a drive of the IV stand assembly, the retainer and fluid container to a predetermined head height on a stand of the IV stand assembly; monitoring, by a weight measurement assembly of the IV stand assembly, a weight of fluid in the fluid container; and moving, by the drive, the retainer and fluid container to a different height on the stand based on the measured weight of the fluid in the fluid container.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
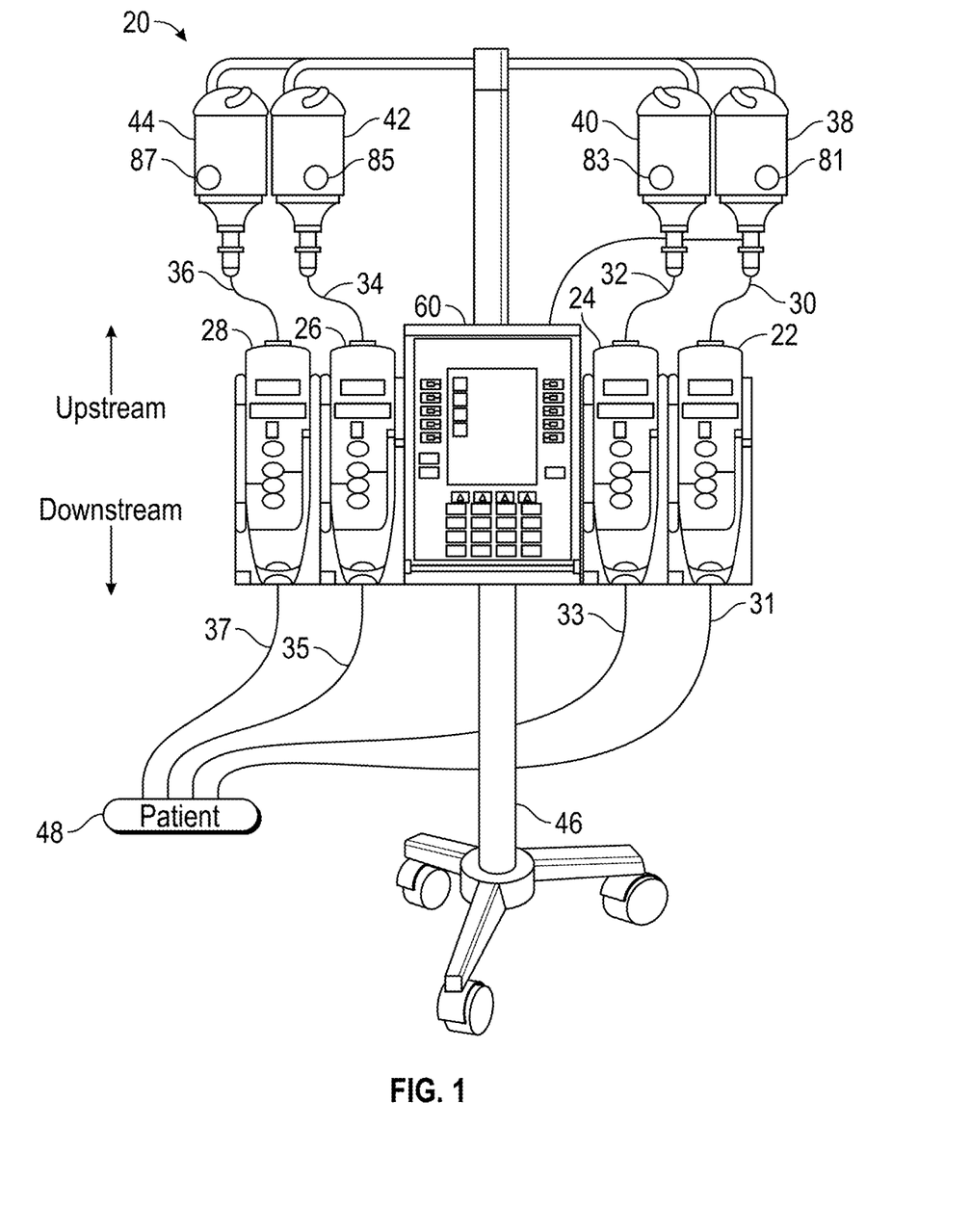
FIG. 1 depicts a perspective view of an example patient care system having four fluid infusion pumps, each of which is connected to a respective fluid supply for pumping the contents of the fluid supply to a patient.

Referring now in more detail to the drawings in which like reference numerals refer to like or corresponding elements among the several views, there is shown in FIG. 1 a patient care system 20 having four infusion pumps 22, 24, 26, and 28 each of which is fluidly connected with an upstream fluid line 30, 32, 34, and 36, respectively. Each of the four infusion pumps 22, 24, 26, and 28 is also fluidly connected with a downstream fluid line 31, 33, 35, and 37, respectively. The fluid lines can be any type of fluid conduit, such as an IV administration set, through which fluid can flow through. It should be appreciated that any of a variety of pump mechanisms can be used including syringe pumps.

Fluid supplies 38, 40, 42, and 44, which may take various forms but in this case are shown as bottles, are inverted and suspended above the pumps. Fluid supplies may also take the form of bags or other types of containers including syringes. Both the patient care system 20 and the fluid supplies 38, 40, 42, and 44 are mounted to an IV pole 46.

A separate infusion pump 22, 24, 26, and 28 is used to infuse each of the fluids of the fluid supplies into the patient. The infusion pumps are flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may include drugs or nutrients or other fluids. The infusion pumps 22, 24, 26, and 28 are controlled by a pump control unit 60.

Fluid supplies 38, 40, 42, and 44 are each coupled to an electronic data tag 81, 83, 85, and 87, respectively, or to an electronic transmitter. Any device or component associated with the infusion system may be equipped with an electronic data tag, reader, or transmitter.

Typical infusion sets may also be gravity sets that do not require use of an infusion pump. For example, any of fluid supplies 38, 40, 42, and 44 may be hung from IV pole 46 and directly connected to the patient 48 via a gravity IV set, wherein gravity causes the fluid to flow through the infusion set and into the patient 48 without the aid of a pump.

A smart IV stand provides novel features to overcome the shortcomings of typical static IV poles. For example, a smart IV stand may include motor-driven IV poles with integrated weight measurement devices on each pole. The motors allow for the IV pole height to be adjusted electronically with high accuracy. The integrated weight measurement devices provide feedback on the amount of fluid/infusate currently hanging on the pole. Additional feedback sensors may be included, such as flow meters to more accurately control infusion rates, for example.

Having motor control on the IV pole creates the ability to control the head-height or pressure inside the IV set. Adjusting the head-height provides a way to control flow rate through an IV set. The flow rate can be made more constant throughout the infusion, or the head-height can be increased or decreased to regulate the desired flow rate.

In addition, motor control on the IV pole provides the ability to raise and lower the height of the pole during loading and unloading of IV containers (e.g., bags, bottles, etc.). Loading IV containers while the IV pole is in a lower position reduces fatigue and may improve the user experience. The weight measurement device may be used as a sensor to identify when an IV container has been properly loaded and the IV pole can then self-adjust to the proper height. Having two motor controlled IV poles provides the ability to raise and lower primary and secondary infusions automatically.

According to aspects of the disclosure, the smart IV stand may provide improvements over the current gravity IV pole systems. For example, the smart IV stand may provide any of flow rate monitoring, flow rate control, automatic primary and secondary set height offsets, predictions of when infusion will be completed, error prevention (e.g., secondary line use, flow rate miscalculations), automatic infusion termination (e.g., IV bag lowers when infusion is complete and prevents air in line), usability (e.g., easier access to bag hook, automatic flow rate feedback with no calculations, eliminate secondary line hangers).

According to aspects of the disclosure, the smart IV stand may also provide any of greater flow rates than a pump (e.g., wide open flow), a priming assist (e.g., low bag height for slow priming rate to prevent air bubbles, then rise to correct height after priming complete), a visual indication of complete infusion (e.g., bag is lowered), occlusion detection (e.g., little or no change in measured IV bag weight over time), and integration with a medical (e.g., hospital) information system.

According to aspects of the disclosure, the smart IV stand may further provide any of higher accuracy, high flow rates, lower system complexity (e.g., lower capital equipment complexity and cost), and lower complexity for consumable components (e.g., no pump interface).

According to aspects of the disclosure, the smart IV stand may provide closed loop flow control via weight sensing, head height adjustment and orifice/clamping control.

As shown in FIGS. 2 through 7, a smart, self-adjusting IV stand 100 is provided, according to aspects of the disclosure. IV stand 100 includes a base 110, a stand 120, pole assemblies 130, a weight measurement assembly 140, fluid source retainers 150 and a display 160.

Figures 2, 3:
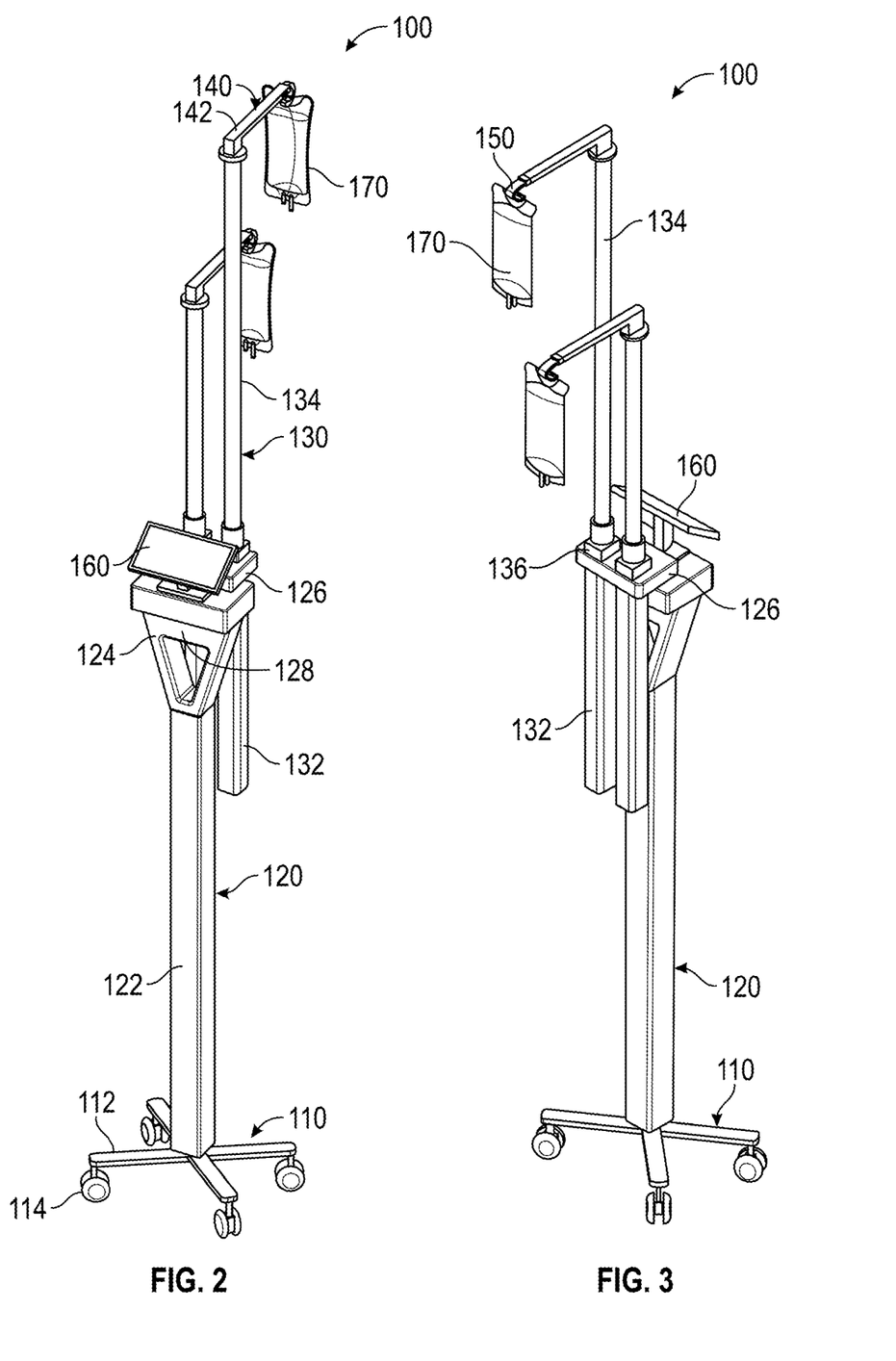
FIG. 2 is a front perspective view of a self-adjusting IV stand, according to aspects of the disclosure.
FIG. 3 is a rear perspective view of the self-adjusting IV stand of FIG. 2, according to aspects of the disclosure.
Figure 4:
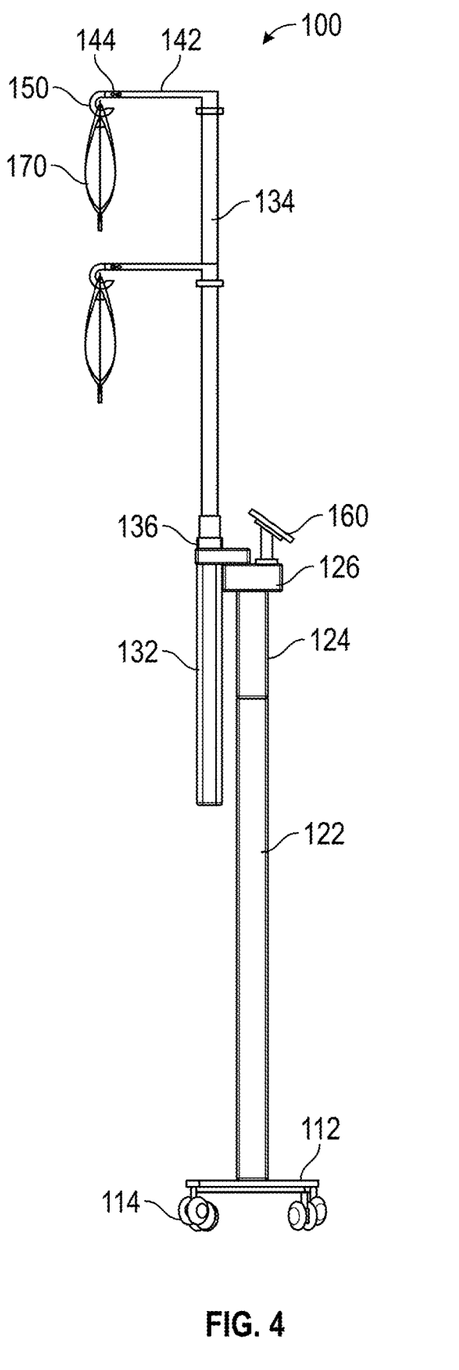
FIG. 4 is a side view of the self-adjusting IV stand of FIG. 2, according to aspects of the disclosure.

The base 110 may include supports 112 and wheels 114, allowing base 110 to be moved/rolled to make the IV stand 100 portable. For example, IV stand 100 may be rolled along a floor, thus allowing the IV stand 100 to be easily moved between storage and treatment areas, or for a patient to be ambulatory by simply moving the IV stand 100 along with the patient as they walk or move in a wheelchair. In some aspects of the disclosure, IV stand 100 may be mounted (e.g., to a wall, bed) or have a stationary stand, for example.

The stand 120 is coupled to the base 110 and may include a square shaped support 122 as shown. In aspects of the disclosure, the support 122 may be any suitable shape (e.g., cylindrical, oval, rectangular, triangular). The stand 120 also includes a head structure 124 and a platform 126. The head structure 124 may be any suitable size and shape for supporting the platform 126. For example, the head structure 124 as shown is an inverse triangular shape with a rectangular platform 126 coupled to the inverted base 128 of the triangular head structure 124. According to aspects of the disclosure, each of the head structure 124 and the platform 126 may be any suitable size and shape (e.g., square, rectangular, oval, circular).

The platform 126 is coupled to the display 160, which may be a passive display for displaying information only or an interactive display (e.g., touchscreen, keypad) providing for user interaction (e.g., data entry, control, changing settings) and display of information (e.g., text, graphics). The platform 126 is also coupled to the pole assemblies 130.

Figure 5:
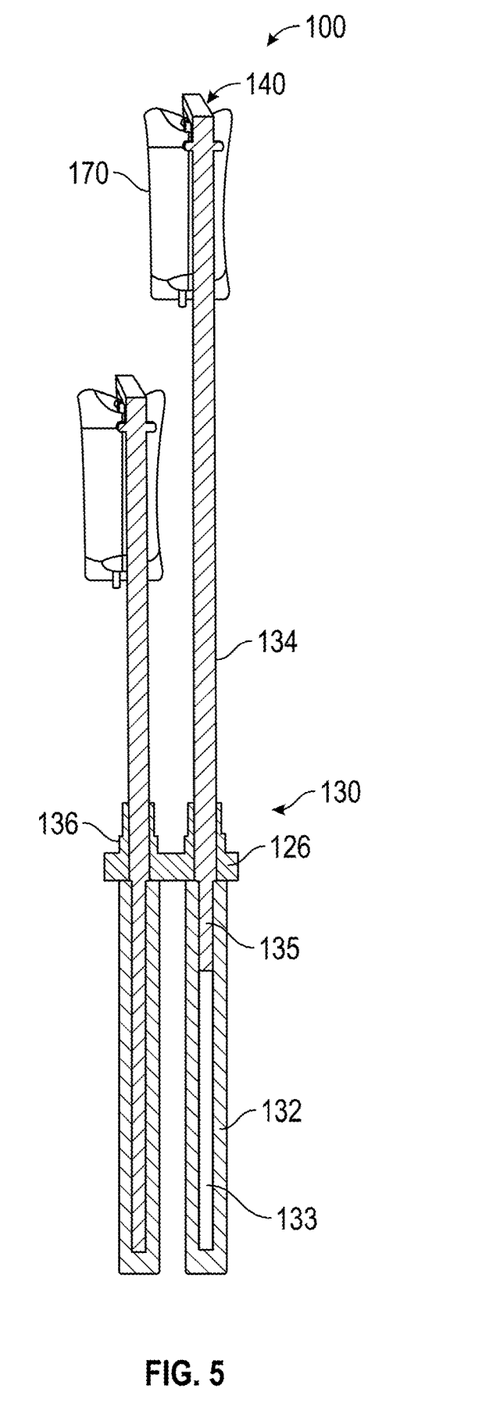
FIG. 5 is a rear cross-sectional view of a top portion of the self-adjusting IV stand of FIG. 2, according to aspects of the disclosure.
Figure 6:
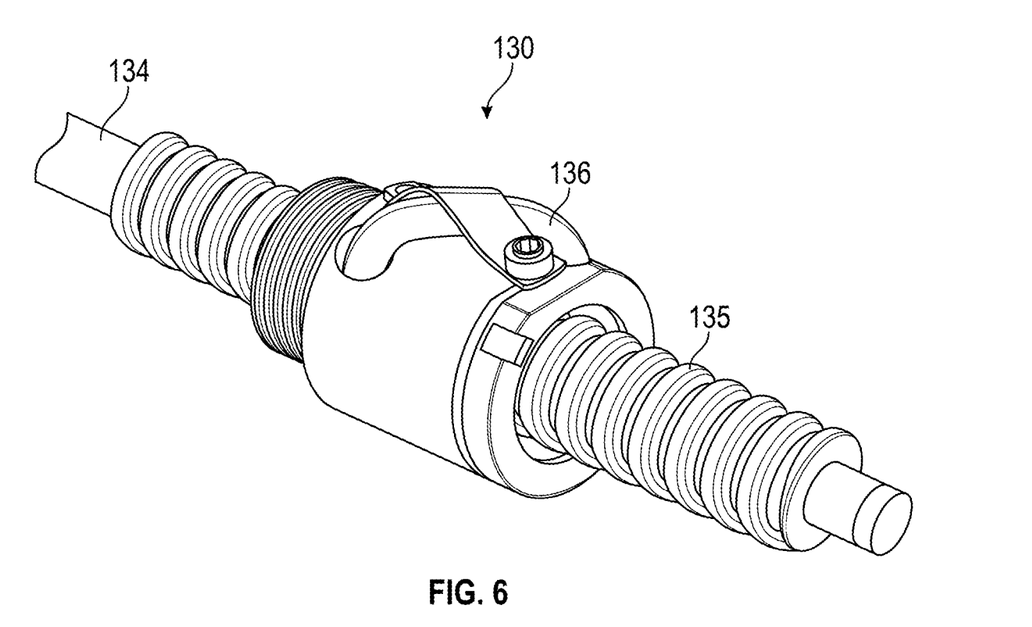
FIG. 6 is a perspective view of a screw-drive motor assembly, according to aspects of the disclosure.

Each pole assembly 130 includes a housing 132, a movable pole 134 and a drive 136. The housing 132 includes a cavity 133 sized and shaped to receive a portion of the pole 134. The housing 132 is also configured to receive or mate with a portion of the drive 136. The drive 136 is configured to move the pole 134 up and down relative to the platform 126. For example, as shown in FIG. 6, a portion of the pole 134 includes a threaded portion 135 and the drive 136 is a screw drive mated with the threaded portion 135 such that operation of the drive 136 causes the threaded portion 135 to wind or unwind to cause the entire pole 134 to move up or down. According to aspects of the disclosure, the drive 136 may be any suitable drive (e.g., induction, magnetic) for moving the pole 134 in a linear fashion.

Figure 7:
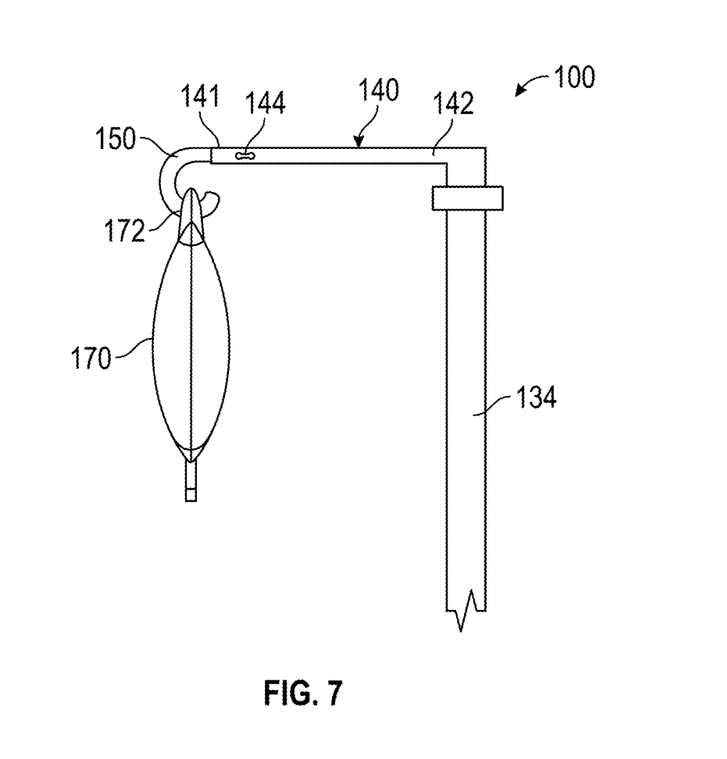
FIG. 7 is a side view of a top portion of the self-adjusting IV stand of FIG. 2, according to aspects of the disclosure.

The weight measurement assembly 140 is coupled to the pole assembly 130, such as a top end of the pole 134 as shown. The weight measurement assembly 140 includes a cross spar 142 that is directly coupled to the pole 134 and a sensor assembly 144. For example, as shown, the sensor assembly 144 may be a level sensor disposed within the cross spar 142. Here, the level sensor 144 may measure an amount of deviation of the orientation of the sensor from a horizontal plane, similar to a level used as a construction tool. Here, the weight of the fluid in a full fluid container 170 may cause the cross spar 142 to flex (e.g., bow downward) and the weight of a fully empty fluid container 170 may put the cross spar 142 in a neutral position (e.g., horizontal, orthogonal to pole). Thus, as the fluid container 170 is drained during operation, the level sensor 144 measures a decreasing amount of flex from full fluid to no fluid, thereby providing a consistent real-time measurement of the amount of fluid in the fluid container 170. In aspects of the disclosure, the sensor assembly 144 may include any suitable sensor (e.g., optical, magnetic, inductive) for monitoring and/or measuring the weight of the fluid in the fluid container 170.

A fluid source retainer 150 is coupled to each weight measurement assembly 140. As shown, the fluid source retainer 150 is a hook coupled to an outer end 141 of the cross spar 142. Here, for example, the fluid container 170 is an IV bag with a mounting hole 172 through which the hook is positioned to hold the IV bag. In aspects of the disclosure, the fluid source retainer 150 may be any suitable retention assembly (e.g., clamp, hanger).

In aspects of the disclosure, the fluid source retainer 150 may interact with the sensor assembly 144. For example, a portion of the fluid source retainer 150 may be movably coupled to the cross spar 142 and/or the sensor assembly 144, such that varying weight in the fluid container 170 causes movement of the fluid source retainer 150 and thus vary the amount of interaction with the sensor assembly 144.

Figure 8:
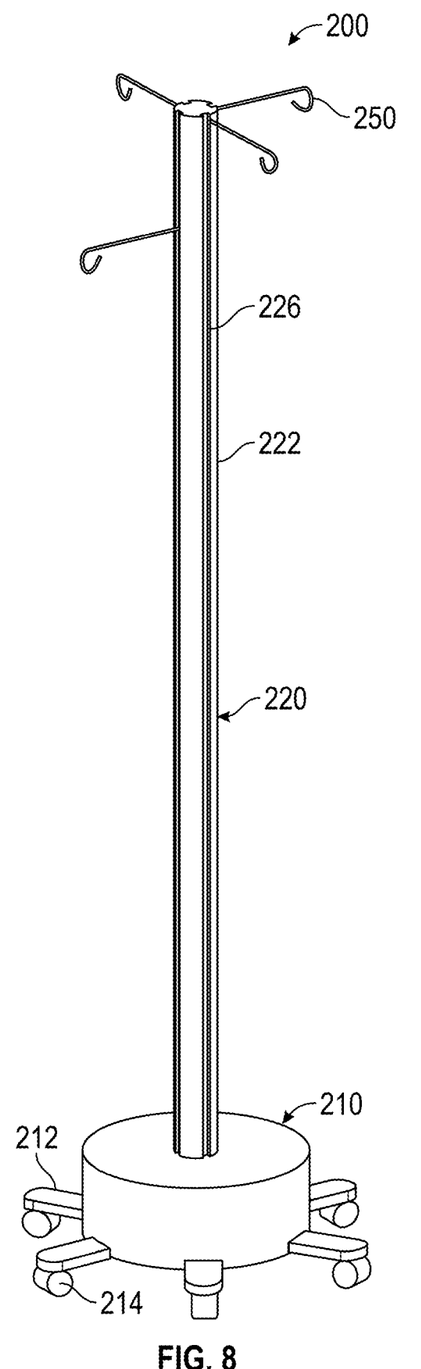
FIG. 8 is a perspective view of a self-adjusting IV stand, according to aspects of the disclosure.
Figure 9:
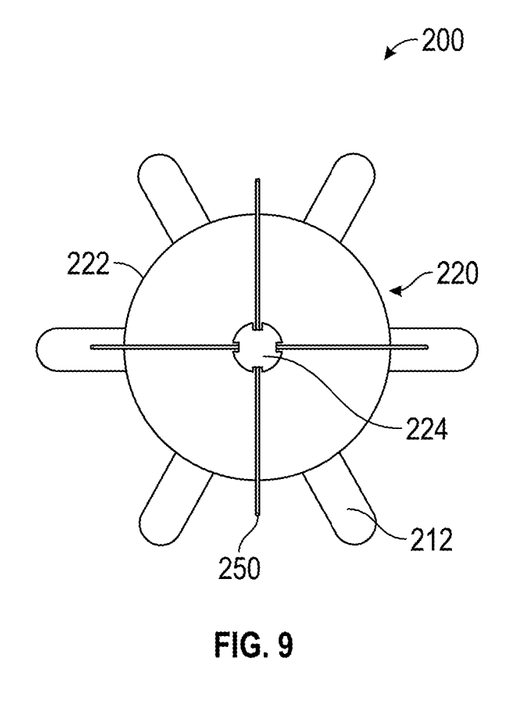
FIG. 9 is a top view of the self-adjusting IV stand of FIG. 8, according to aspects of the disclosure.
Figure 10:
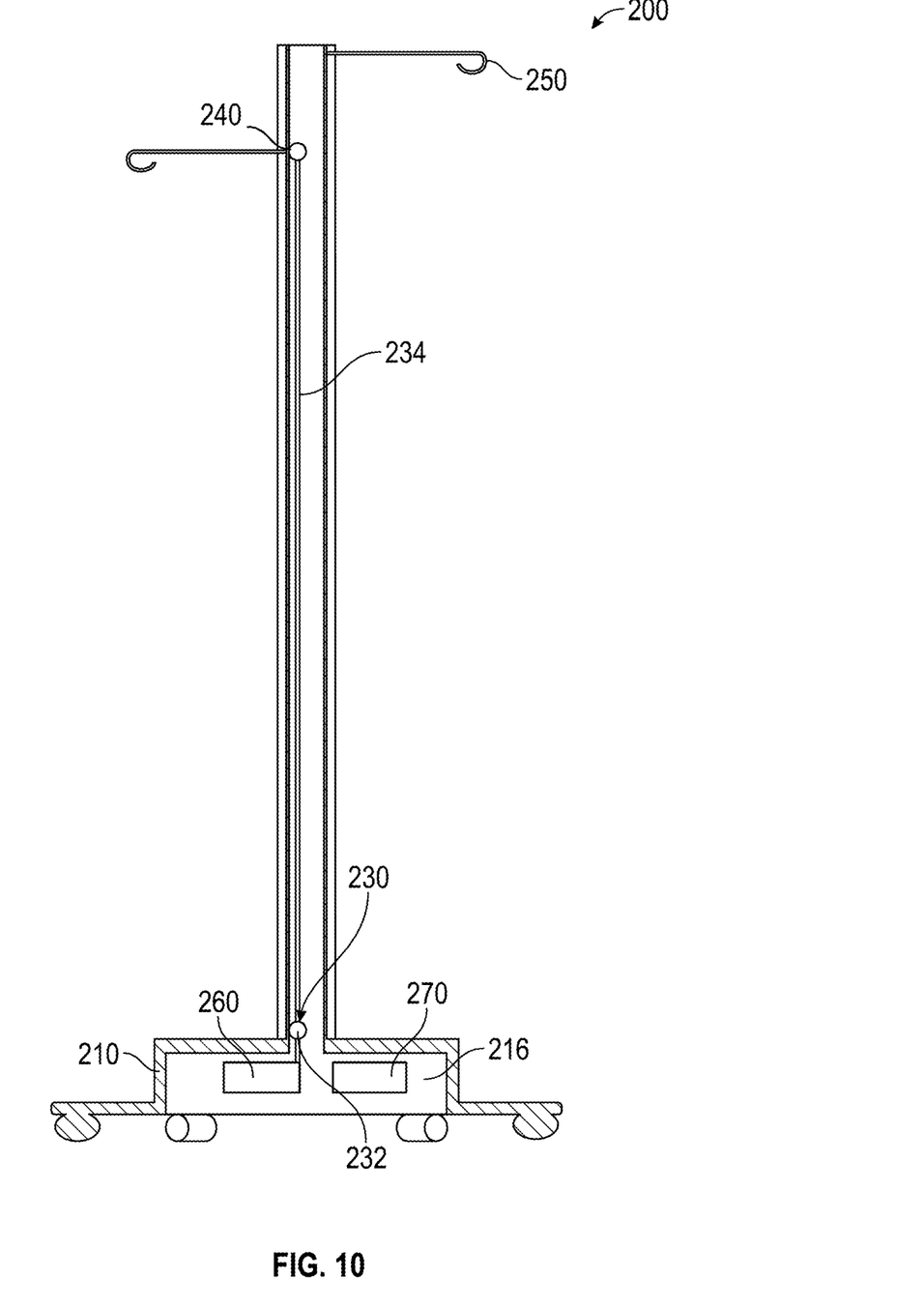
FIG. 10 is a rear cross-sectional view of the self-adjusting IV stand of FIG. 8, according to aspects of the disclosure.

As shown in FIGS. 8 through 10, an IV stand 200 is provided, according to aspects of the disclosure. IV stand 200 includes a base 210, a stand 220, a pulley/belt assembly 230, a weight measurement assembly 240, fluid source retainers 250, a drive 260 and an energy source 270.

The base 210 may include supports 212 and wheels 214, allowing base 210 to be moved/rolled to make the IV stand 200 portable. For example, IV stand 200 may be rolled along a floor, thus allowing the IV stand 200 to be easily moved between storage and treatment areas, or for a patient to be ambulatory by simple moving the IV stand 200 along with the patient as they walk or move in a wheelchair. In some aspects of the disclosure, IV stand 200 may be mounted (e.g., to a wall, bed) or have a stationary stand, for example. In addition, the base 210 has a cavity 216 configured to receive the drive 260 (e.g., motor) and the energy source 270 (e.g., battery) coupled to the drive 260.

The stand 220 is coupled to the base 210 and may include a round shaped support 222 as shown. In aspects of the disclosure, the support 222 may be any suitable shape (e.g., oval, square, rectangular, triangular). The stand 220 also includes an internal channel 224 and retainer channels 226.

The internal channel 224 is configured to receive the pulley/belt assembly 230 and the retainer channels 226 are each configured to movably receive a fluid source retainer 250.

In aspects of the disclosure, the drive 260 is coupled to the pulley/belt assembly 230, where the pulley/belt assembly 230 includes a pulley 232 and a belt 234 for each retainer channel 226. A fluid source retainer 250 (e.g., hook) is coupled to each belt 234, such that when the drive 260 causes movement of a belt 234 relative to the associated pulley 232, the fluid source retainer 250 is moved along the retainer channel 226 (e.g., up and down a length of the stand 220). For example, as shown in FIG. 8, the retainer channels 226 extend along the entire length of the stand 220, thus allowing the fluid source retainers 250 to travel between the top and bottom of the stand 220.

In aspects of the disclosure, the retainer channels 226 may be disposed along any portion of the stand 220 (e.g., top to mid-point). In aspects of the disclosure, any suitable number of retainer channels 226 and associated pulleys 232/belts 234 may be included in IV stand 200. For example, as shown in the figures, the IV stand 200 has four retainer channels 226 supporting four fluid source retainers 250 and thus may handle four fluid containers (e.g., fluid container 170).

In aspects of the disclosure, weight measurement assembly 240 may include a level sensor coupled to the fluid source retainer 250 and configured to measure an amount of deviation of the orientation of the sensor from a horizontal plane, similar to sensor assembly 144 described above. In aspects of the disclosure, the weight measurement assembly 240 may include any suitable sensor (e.g., optical, magnetic, inductive) for monitoring and/or measuring the weight of the fluid in the fluid container 170.

Figure 11:
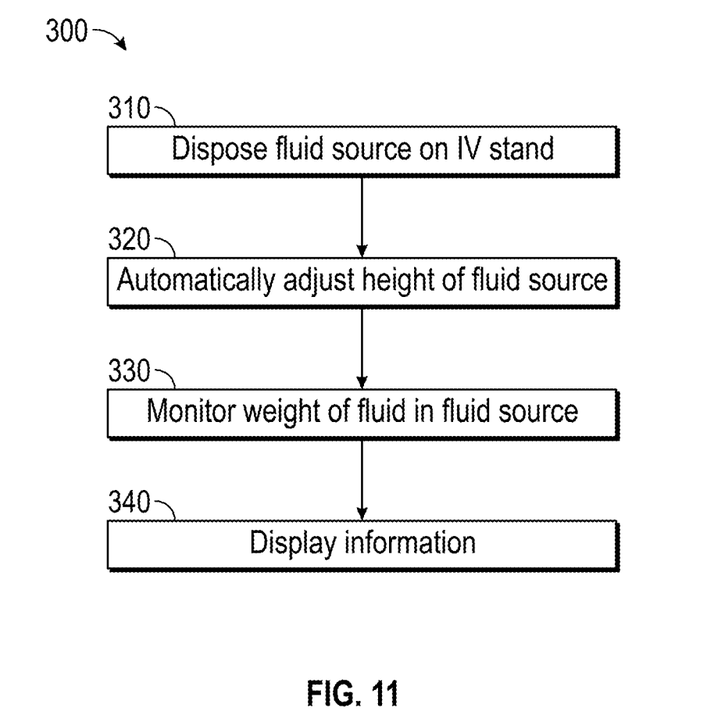
FIG. 11 illustrates a method of operating an IV stand, according to aspects of the disclosure.

According to some aspects of the disclosure, a method 300 of using an IV stand (e.g., IV stand 100, 200) is shown in FIG. 11. In step 310, an IV fluid source (e.g., fluid container 170) is disposed on or attached to a fluid source retainer (e.g., fluid source retainer 150, 250). In aspects of the disclosure, the fluid source retainer may be an IV bag or an IV bottle and the fluid source retainer may be a hook.

The height of the fluid source is adjusted in step 320. In aspects of the disclosure, the IV stand may lower the fluid source retainer so that the IV fluid source may be easily hung, and then automatically raise the fluid source retainer and IV fluid source to the desired head height on the IV stand. In aspects of the disclosure, the height of the IV fluid source may be adjusted by a drive mechanism (e.g., pole assembly 130 and drive 136, pulley/belt assembly 230 and drive 260). In aspects of the disclosure, the height of the IV fluid source may be continuously adjusted as the fluid is drained or removed from the IV fluid source (e.g., the hook is continuously lowered as the fluid leaves the fluid container). In this respect, the height of the IV fluid source provides an instant visual indication of the amount of fluid left to be administered.

In step 330, the weight of the fluid in the fluid source is monitored. For example, a sensor assembly (e.g., weight measurement assembly 140, 240) may be coupled to the fluid source retainer such that weight of the fluid in the IV fluid source may be measured or determined. In aspects of the disclosure, the weight of the fluid in the IV fluid source may be measured at intervals or continuously.

Information pertaining to the monitored weight is displayed in step 340. For example, instructions and/or an alert may be displayed on a display (e.g., display 160) of the IV stand. The information may indicate that the IV fluid source is empty or will be empty in a certain period of time.

In one or more embodiments, an IV stand assembly, comprises: a base; a stand coupled to the base; a platform disposed at an end of the stand; and a motorized pole assembly coupled to the platform. The motorized pole assembly comprises: a housing; a pole movably coupled to the housing; and a drive coupled to the pole, the drive configured to move the pole to extend and retract the pole relative to the housing. The IV stand assembly further comprises a weight measurement assembly coupled to the pole assembly, the weight measurement assembly configured to measure weight of a fluid within a fluid container hanging from the IV stand assembly.

In aspects of the disclosure, the drive is a screw drive disposed within the housing and configured to movably engage with a threaded portion of the pole disposed within the housing to linearly move the pole forwards and backwards relative to the housing. In aspects of the disclosure, the drive is an induction drive disposed within the housing and configured to movably engage with a portion of the pole disposed within the housing to linearly move the pole forwards and backwards relative to the housing. In aspects of the disclosure, the drive is a magnetic drive disposed within the housing and configured to movably engage with a portion of the pole disposed within the housing to linearly move the pole forwards and backwards relative to the housing.

In aspects of the disclosure, a display is coupled to the platform, the display configured to one of display information and provide for user input. In aspects of the disclosure, the weight measurement assembly comprises a cross spar coupled to an end of the pole and a sensor assembly. In aspects of the disclosure, the sensor assembly comprises a level sensor disposed within the cross spar, the level sensor configured to measure an amount of flex of the cross spar. In aspects of the disclosure, a retainer is coupled to the weight measurement assembly, the retainer configured to couple to and support a fluid container.

In aspects of the disclosure, the retainer is movably coupled to one of the cross spar and the sensor assembly, the retainer configured to move in response to a change in weight of the fluid container, wherein the movement of the retainer causes a variation in interaction with the sensor assembly. In aspects of the disclosure, the motorized pole assembly is a first motorized pole assembly and the weight measurement assembly is a first weight measurement assembly, wherein the IV stand assembly further comprises a second motorized pole assembly coupled to the platform adjacent to the first motorized pole assembly, the first and second motorized pole assemblies configured to operate independently from each other and a second weight measurement assembly coupled to the second motorized pole assembly, wherein the first and second measurement assemblies are configured to measure the weight of separate fluid containers.

In one or more embodiments, an IV stand assembly, comprises: a base; a stand coupled to the base, the stand comprising an internal channel and a retainer channel; a pulley/belt assembly disposed within the internal channel of the stand, the pulley/belt assembly comprising a pulley and a belt; a retainer coupled to the belt, the retainer movably disposed within the retainer channel; and a drive coupled to the belt, the drive configured to move the belt relative to the pulley to cause the retainer to move along the retainer channel.

In aspects of the disclosure, the drive is disposed within the base. In aspects of the disclosure, an energy source is coupled to the drive, the energy source disposed within the base. In aspects of the disclosure, a plurality of wheels are coupled to the base. In aspects of the disclosure, a weight measurement assembly is coupled to the retainer, the weight measurement assembly configured to measure weight of a fluid within a fluid container hanging from the retainer. In aspects of the disclosure, the weight measurement assembly comprises a level sensor coupled to the retainer, the level sensor configured to measure an amount of flex of the retainer.

In aspects of the disclosure, the retainer channel extends between an end of the stand adjacent to the base to an opposing end of the stand. In aspects of the disclosure, the stand comprises a plurality of retainer channels and the pulley/belt assembly comprises a plurality of pulleys and belts, and the IV stand assembly further comprises a plurality of retainers, each of the plurality of retainers disposed in one of the plurality of retainer channels and coupled to one of the plurality of belts, wherein each of the plurality of belts is coupled to the drive, wherein each of the plurality of belts is coupled to a separate one of the plurality of pulleys, and wherein each of the retainers is separately moveable.

In one or more embodiments, a method of operating an IV stand assembly comprises: hanging a fluid container on a retainer of the IV stand assembly; moving, by a drive of the IV stand assembly, the retainer and fluid container to a predetermined head height on a stand of the IV stand assembly; monitoring, by a weight measurement assembly of the IV stand assembly, a weight of fluid in the fluid container; and moving, by the drive, the retainer and fluid container to a different height on the stand based on the measured weight of the fluid in the fluid container.

In aspects of the disclosure, the method further comprises moving the retainer to a lower height on the stand prior to hanging the fluid container on the retainer; automatically moving the retainer and fluid container to the predetermined head height after the fluid container is hung from the retainer; and automatically moving the retainer and fluid container to a different height on the stand when the weight of the fluid in the fluid container changes.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, inserting and the like via a hardware element.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An intravenous (IV) stand assembly, comprising:
   a base;
   a stand coupled to the base;
   a platform disposed at an end of the stand;
   a first motorized pole assembly coupled to the platform, the first motorized pole assembly comprising:
      a first housing;
      a first pole movably coupled to the first housing; and
      a first drive coupled to the first pole, the first drive configured to move the first pole to extend and retract the first pole relative to the first housing;
   a first weight measurement assembly coupled to the first pole motorized assembly, the first weight measurement assembly configured to measure weight of a fluid within a first fluid container hanging from the IV stand assembly;
   a second motorized pole assembly coupled to the platform, the second motorized pole assembly comprising:

a second housing;

a second pole movably coupled to the second housing; and a second drive coupled to the second pole, the second drive configured to move the second pole to extend and retract the second pole relative to the second housing; and a second weight measurement assembly coupled to the second motorized pole assembly, the second weight measurement assembly configured to measure weight of a fluid within a second fluid container hanging from the IV stand assembly, wherein the first and second motorized pole assemblies are configured to operate independently from each other.

2. The IV stand assembly of claim 1, wherein the first drive is a screw drive disposed within the first housing and configured to movably engage with a threaded portion of the first pole disposed within the first housing to linearly move the first pole upwards and downwards relative to the first housing.

3. The IV stand assembly of claim 1, wherein the first drive is an induction drive disposed within the first housing and configured to movably engage with a portion of the first pole disposed within the first housing to linearly move the first pole upwards and downwards relative to the first housing.

4. The IV stand assembly of claim 1, wherein the first drive is a magnetic drive disposed within the first housing and configured to movably engage with a portion of the first pole disposed within the first housing to linearly move the first pole upwards and downwards relative to the first housing.

5. The IV stand assembly of claim 1, further comprising a display coupled to the platform, the display configured to one of display information and provide for user input.

6. The IV stand assembly of claim 1, wherein the first weight measurement assembly comprises:

a cross spar coupled to an end of the first pole; and a sensor assembly.

7. The IV stand assembly of claim 6, wherein the sensor assembly comprises a level sensor disposed within the cross spar, the level sensor configured to measure an amount of flex of the cross spar.

8. The IV stand assembly of claim 6, further comprising a retainer coupled to the first weight measurement assembly, the retainer configured to couple to and support a fluid container.

9. The IV stand assembly of claim 8, wherein the retainer is movably coupled to one of the cross spar and the sensor assembly, the retainer configured to move in response to a change in weight of the fluid container, wherein the movement of the retainer causes a variation in interaction with the sensor assembly.

10. A method of operating an intravenous (IV) stand assembly, the method comprising:

hanging a fluid container on a retainer of the IV stand assembly;

moving, by a drive of the IV stand assembly, the retainer and fluid container to a predetermined head height on a stand of the IV stand assembly;

monitoring, by a weight measurement assembly of the IV stand assembly, a weight of fluid in the fluid container; and moving, by the drive, the retainer and fluid container to a different height on the stand based on the measured weight of the fluid in the fluid container.

11. The method of claim 10, further comprising:

moving the retainer to a lower height on the stand prior to hanging the fluid container on the retainer;

automatically moving the retainer and fluid container to the predetermined head height after the fluid container is hung from the retainer; and automatically moving the retainer and fluid container to a different height on the stand when the weight of the fluid in the fluid container changes.

* * * * *